United States Patent [19]

Bradwell et al.

[11] Patent Number: 4,889,815

[45] Date of Patent: Dec. 26, 1989

[54] NEPHELOMETRIC METHOD FOR DETERMINATION OF AN ANTIGEN OR ANTIBODY CONTENT IN WHOLE BLOOD

[75] Inventors: Arthur R. Bradwell, Birmingham; Ian Deverill, Mansfield, both of England

[73] Assignee: Alta Diagnostic Machines Limited, Birmingham, England

[21] Appl. No.: 922,359

[22] Filed: Oct. 23, 1986

[30] Foreign Application Priority Data

Oct. 25, 1985 [GB] United Kingdom ................. 8526355

[51] Int. Cl.[4] .................. G01N 33/536; G01N 33/557
[52] U.S. Cl. ..................................... 436/517; 436/536; 436/805; 436/825; 436/909
[58] Field of Search ............... 436/517, 536, 805, 825, 436/909, 518

[56] References Cited

U.S. PATENT DOCUMENTS

| | | | |
|---|---|---|---|
| 4,080,264 | 3/1978 | Cohen et al. | 436/805 |
| 4,204,837 | 5/1980 | Sternberg | 23/230 B |
| 4,284,412 | 8/1981 | Hansen et al. | 436/805 |
| 4,305,925 | 12/1981 | Kapmeyer et al. | 436/805 |
| 4,401,387 | 8/1983 | Tokinage et al. | 356/341 |
| 4,690,906 | 9/1987 | Duheille et al. | 436/517 |

FOREIGN PATENT DOCUMENTS

| | | |
|---|---|---|
| 0091636 | of 0000 | European Pat. Off. |
| 3026077 | of 0000 | Fed. Rep. of Germany |
| 2488409 | of 0000 | France |
| 60-47962 | 3/1985 | Japan |

OTHER PUBLICATIONS

IEEE Transactions on Bio-Medical Engineering, vol. BME-17, No. 2, Apr. 1970, pp. 129-133, IEEE, New York, US: C. C. Johnson: "Optical Diffusion in Blood."
Whicher et al., In Butt (Ed.) *Practical Immunoassay*, Marcel Dekker, Inc., New York, 1984. p. 151.
Whicher et al., In Butt (Ed.), *Practical Immunoassay,,-* Marcel Dekker, Inc., New York, 1984, pp. 143-144.

*Primary Examiner*—Robert J. Warden
*Assistant Examiner*—David A. Saunders
*Attorney, Agent, or Firm*—Nixon & Vanderhye

[57] ABSTRACT

A method and apparatus for use in quantifying, in a whole blood sample in which the red cells are lysed, a component which will react with a reagent to form an antigen-antibody complex, the method comprising mixing the sample with the reagent to obtain the complex, exposing the sample to a source of radiation and measuring the intensity of radiation scattered through a given angle by the complex, and the apparatus including a container for receiving the sample which has been treated with the reagent to the component, the container being transparent to radiation having a wavelength falling within a given band width, typically 460-530 nm. A source of radiation within this band width is provided together with a device for detecting the intensity of radiation scattered through a given angle by the sample.

10 Claims, 5 Drawing Sheets

NEPHELOMETRIC METHOD FOR DETERMINATION OF AN ANTIGEN OR ANTIBODY CONTENT IN WHOLE BLOOD

The present invention relates to a method of determining the content of a component in a sample of blood, particularly the antigen or antibody content of a sample of whole blood.

Previously proposed methods of determining the antigen content of a sample of blood involve forming a complex between the antigen to be determined and marker antibodies to form agglomerates. These agglomerates will scatter incident radiation and by measuring the intensity of the scattered radiation, the concentration of complex agglomerates, and hence the concentration of antigen can be determined. Typically, the incident radiation has had a wavelength in the ultra-violet part of the spectrum, usually at 290–340 nm where the scattering signal is strong.

However, this method suffers from the problems that there is also a strong scattering at these wavelengths by haemoglobin, and the red blood cells themselves absorb and scatter radiation both of which interfere with the signal from the antigen/antibody agglomerates. Consequently, it has been considered necessary to remove the red blood cells by centrifuging in which case the time taken from obtaining the blood sample to obtaining the results of the analysis is relatively long. Also the use of radiation in the ultra-violet part of the spectrum requires a stable power source to be used which is bulky and requires mains electricity.

It is an object of the present invention to obviate or mitigate the problems outlined above and provide a method of determining the antibody content of whole blood which can be carried out quickly, and in the absence of a mains power supply.

It has been previously proposed to carry out immunological and other blood analyses using a nephelometer. It has also been proposed to utilize a flash light source such as a xenon flash (No. DE-A-3020677) in such a nephelometer. However, the previously proposed designs of nephelometer suffer from the problems that they are intended for use with existing methods of blood analysis and consequently utilize wavelengths of radiation which either require stabilized power supplies, e.g. ultra violet wavelengths, or wavelengths which would be absorbed by haemoglobin and so require separation of red blood cells or haemoglobin from a blood sample if they are to be useful.

If is a further object of the present invention to provide a nephelometer which can be used to analyse samples of whole blood without the need to remove red blood cells or haemoglobin.

In accordance with a first aspect of the present invention there is provided a method of quantifying, in a whole blood sample in which the red cells are lysed, a component which will react with a reagent to form an antigen-antibody complex, comprising mixing said sample with said reagent to obtain said complex, exposing said sample to a source of radiation and measuring the intensity of radiation scattered through a given angle by said complex.

In a particular embodiment the intensity of said scattered radiation is measured at intervals, to determine the rate of formation of said antigen-antibody complex.

Preferably, the wavelength of the radiation is selected such that it is a wavelength at which the intensity of the radiation scattered through said angle by the antigen/antibody complex is high and the absorption of said radiation by haemoglobin and other proteins is low. It is particularly preferred that the intensity of the scattered radiation is at a local maximum and the absorption of the radiation is at a local minimum.

Typical wavelengths of suitable radiation are 460–530 nm, more preferably 460–510 mn. The red cells are lysed such that they fragment into particles of a size which does not scatter light of these wavelengths and so reduces interference.

Because the methods described in the previous aspects of the present invention do not require centrifuging or an ultraviolet light source and its attendant power supply, it is possible to construct the apparatus for carrying out these methods such that it is portable and relies on an internal power supply.

According to a further aspect of the present invention, there is provided an apparatus for quantifying an antigen/antibody complex in a whole blood sample in which the red cells have been lysed, including means for receiving said sample which has been treated with a reagent which forms an antigen/antibody complex with a component of the sample, said means being transparent to radiation having a wavelength falling within a given band width, typically 460–530 nm, a source of radiation having a radiation within said band width and means for detecting the intensity of said radiation which is scattered through a given angle by the sample.

Preferably, the apparatus is portable and it is also preferred that the radiation source is a xenon flash tube powered by a dry cell battery. The duration of the flash mat be controlled automatically by means of a sensor which monitors the amount of light reflected or transmitted by the sample and which is connected to the source to terminate the flash when sufficient light has been reflected. More particularly, the amount of haemoglobin in the sample is measured by measuring the light transmitted by the sample at a wavelength corresponding to a haemoglobin absorption peak and this measurement is used to control the duration of the flash and so compensate for the red blood cells content of the sample.

The present invention will now be described, by way of example, with reference to the accompanying drawing in which.

Figure 1:
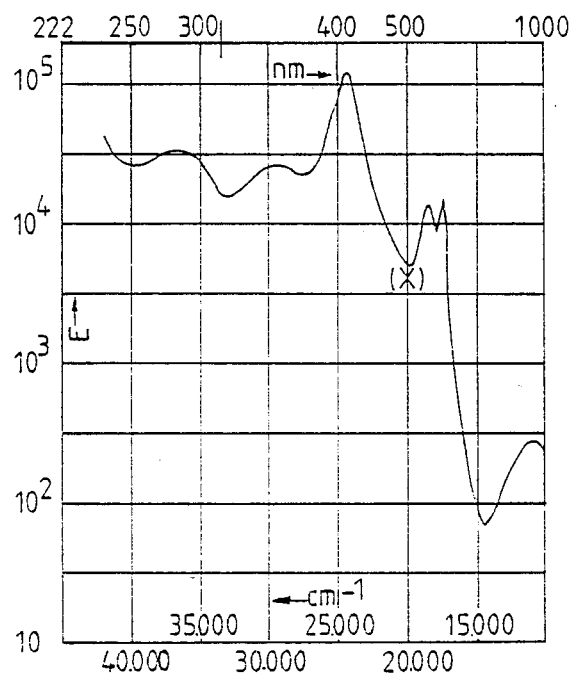
FIG. 1 is a chart showing the spectrum of haemoglobin

In an example of the present invention, the apparatus comprises a high intensity light source comprising a xenon flash discharge tube 10, such as is typically used in photography powered by a small dry cell. This tube, in conjunction with interference filters and suitable attenuation means 11, 12, gives a narrow band width source of radiation with a maximum at 479 mn. The filters are desired to give a maximum at 473 but production defects may cause a small shift of a few nm from this filter to filter.

Alternatively, a high intensity output light emitting diode can be used. This has the advantage that the wavelength of the emitted light (e.g. 480 nm) can be controlled quite accurately and so reduces the need for extensive filtering.

A cuvette 13 is charged with 3.0 ml of physiological saline/4 percent polyethylene glycol, 20 $\mu$l of zaponin/KCN (available from Ortho Pharmaceutical) and 5 ml of whole blood. 40 $\mu$l of anti IgG antiserum is added to this mixture. It is possible to increase the sensitivity of the method according to the present invention by using particle bound antibodies e.g latex bound antibodies which cause agglomerates to form which scatter radiation more effectively.

The cuvette 13 is made from a suitable transparent material and is placed in the path of the light 16 from the flash tube 10. Because it is not necessary to effect any pre-treatment to the blood sample before it is introduced into the cuvette, it is possible to reduce the amount of handling of the sample to a minimum. This reduces any contact the operator may have with the blood sample to a minimum and so increases the safety of the present method and apparatus.

A photo diode detector 14 is arranged to receive any light 17 which is scattered through a given angle from the sample, in the present case the angle is 90°. The interference filters 11 are placed between the flash tube 10 and the detector 14 such that only light of a specified wavelength is transmitted to the detector 14.

A further detector 15 is positioned to detect light 18 transmitted by the sample at a given wavelength (selected by means for further filters 20) corresponding to haemoglobin absorption. This detector 15 is linked via control circuitry 19 to the flash tube 10 and terminates the flash when sufficient light has been received. This automatically compensates for the red blood cell content of the sample and is not necessary in certain applications of the present invention.

For instance, when it is desired to find the concentration of a particular protein in a sample of whole blood compensation may be needed, whereas if it is desired to find only the concentration of a protein in the serum of a sample the reading no correction for haemoglobin content is required.

Figure 3:
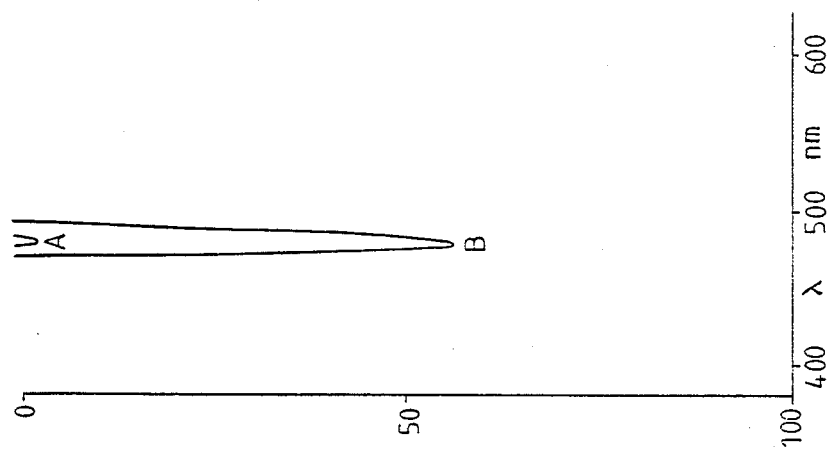
FIG. 3 is a scan showing the relative light scattering, in arbitrary units, of the solutions scanned in lines A and B of FIG. 2.
Figure 2:
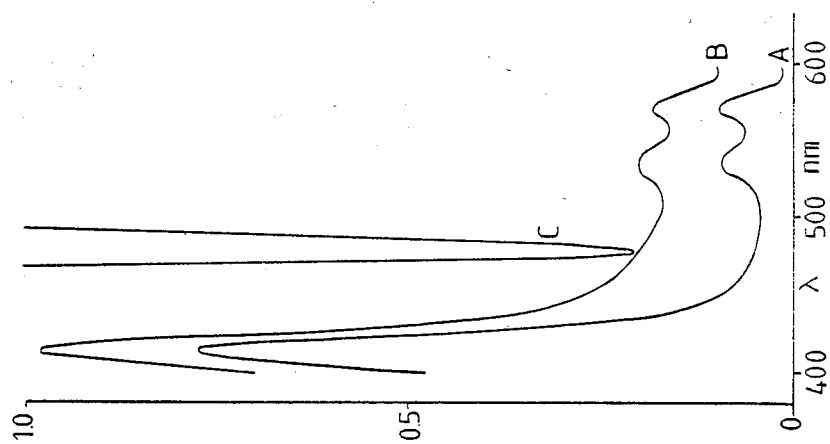
FIG. 2 is a spectrophotometer scan of a cuvette containing saline, polyethylene glycol, zaponin/KCN and whole blood (line A); the same cuvette two minutes after the addition of anti IgG antiserum (line B); and the interference filter employed in the device described below (line C)

Referring now to FIGS. 1-3, the wavelength of light used is chosen such that the signal from the complex is relatively high and the signal from haemoglobin is at a relative minimum (x) and the total signal relative to background signal is as strong as possible. This is done to ensure that the strength of the signal obtained is mainly effected by the concentration of the complex rather than other incidental factors. In the present case the wavelength chosen is 473 nm ($\pm$ a few nm due to variations between filters). The detector 14 is linked to a calibrated display 21 such that the signal may be directly displayed in terms of antigen concentration.

Figure 4:
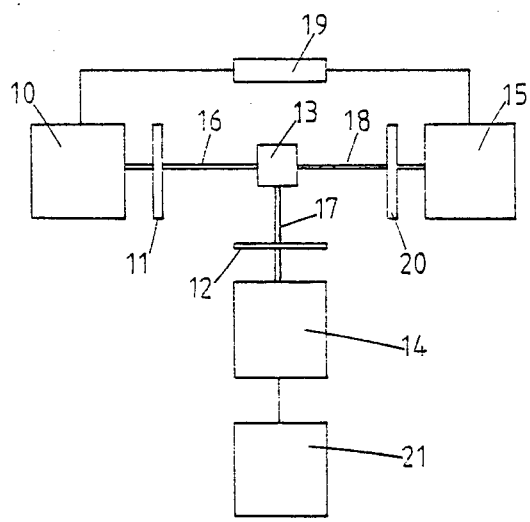
FIG. 4 is a block diagram of an apparatus according to an aspect of the present invention.
Figure 5:
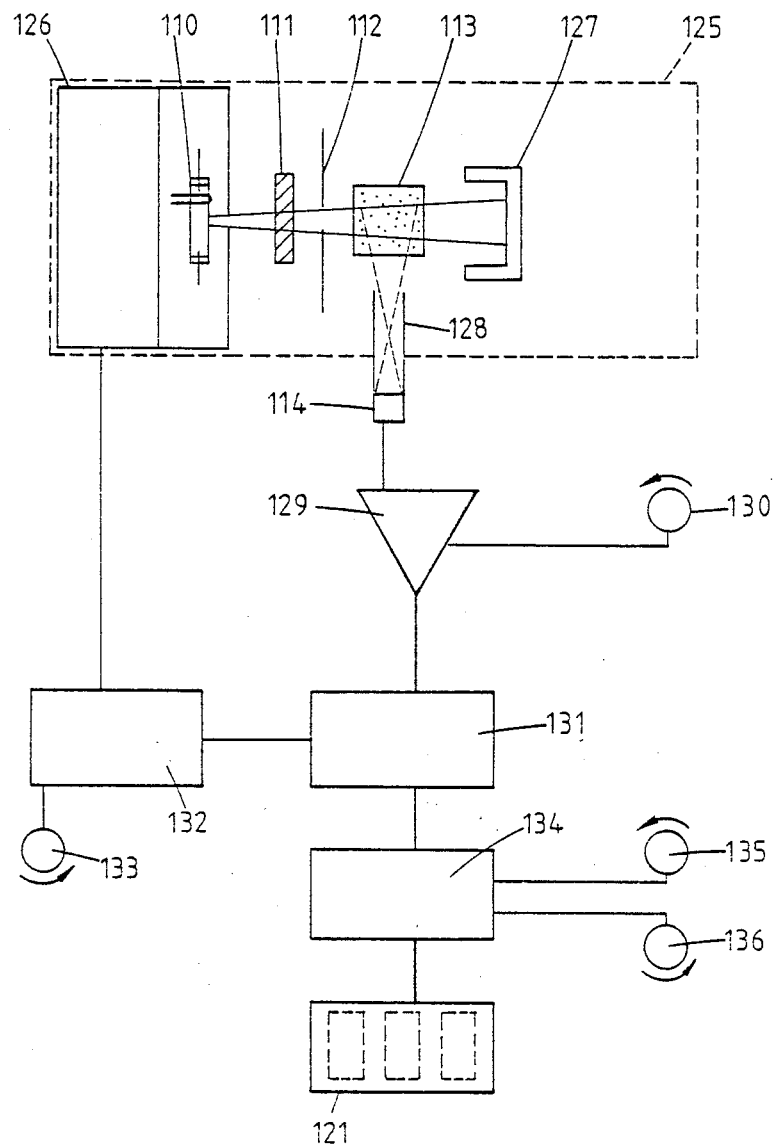
FIG. 5 is a block diagram of an apparatus according to the present invention for carrying out simple analyses.

Referring now to FIG. 5 those parts which are the same as shown in FIG. 4 are given the same reference numerals in the 100 series. Located within an optical chamber 125 are flash charge and trigger circuitry located within a screened compartment 126 controlling activation of the xenon discharge tube 110, said tube 110, interference filter and illumination aperture 111 and 112, the sample 113, a light sink 127 and the detector 114 in a scatter aperture pipe 128. The light sink 127 serves to absorb any light which is transmitted by the sample and so prevent any reflections within the chamber 125 which may affect the readings. The detector 114 and aperture pipe 128 are arranged in such a way that only light which has been scattered through substantially 90° falls upon the detector 114. The detector 114 emits a signal to a detector amplifier 129 which has means 130 for adjusting the gain on the amplifier 129 and hence allows adjustment of the sensitivity of the apparatus.

A signal from the amplifier 129 is taken to a peak detector 131 which is connected to a timing circuit 132 provided with adjustment means 133. The timing circuit is also connected to the trigger circuitry in compartment 126. The timing circuit 132 controls the activation of the tube 110 and the peak detector 131. Activation of the timing circuits 132 causes the tube to discharge at a given time after the immunochemical reaction has been initiated in the cuvette 113. The peak detector 131 is activated a short time after the tube 110 is discharged in order to eliminate any e.m.f. peak effects caused by the discharge. The peak detector 131 continues to function until a peak is reached when no more readings are taken.

The signal from the peak detector 131 is fed into a digital multimeter 134 which is provided with controls for zeroing 135 and calibration 136. The readings from the multimeter are shown on a digital display 121.

This apparatus does not cater for compensation for differences between test blanks or in differences in haemoglobin level between samples.

However, such an apparatus can be used satisfactorily in application for detecting the presence or absence of a factor in the sample.

Activation of the timing circuits 132 may be achieved manually by operating a switch when the cuvette 113 has been inserted, or insertion of the cuvette 113 can cause automatic operation by use of a micro-switch.

Figure 6:
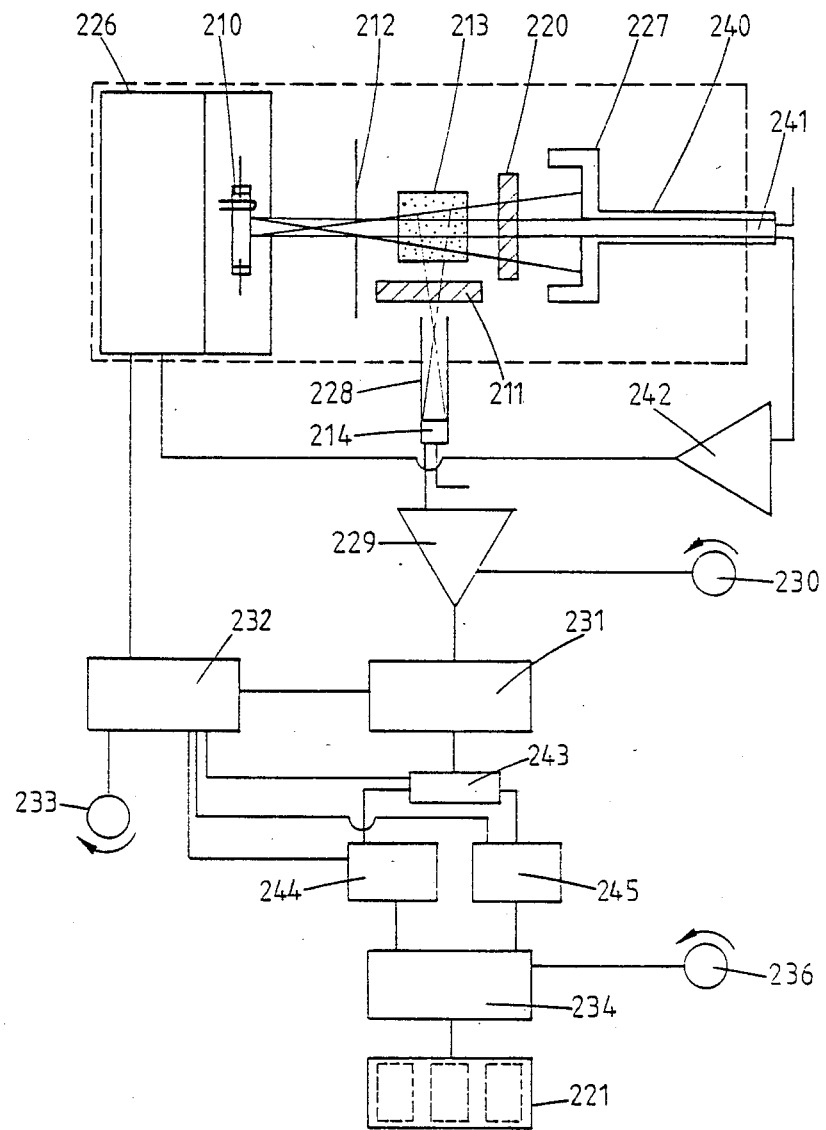
FIG. 6 is a block diagram of a further apparatus according to the present invention for carrying out more accurate analyses.

Referring now to FIG. 6 those parts which correspond to those shown in previous drawings are given the same reference numerals in the 200 series. In this embodiment, the interference filter 211 is located between the cuvette 213 and the detector 214. A further interference filter 220 is located between the cuvette 213 and the light sink 227. A transmission aperture pipe 240 having a further detector 241 therein is provided in the light sink 227 and is arranged to receive light which has been transmitted through the sample. The signal from the further detector 241 is passed to an associated amplifier 242 which in turn sends a signal to the flash change and trigger circuitry. This arrangement is used to control the duration of the flash in order to compensate for the amount of light absorbed by the haemoglobin in the sample.

The signal from the detector 214 is fed to a peak detector 231 via an amplifier 229 as before, the peak detector being controlled by timing circuitry 232. However, the output from the peak detector is fed through a two-way switch 243 to either a first sample and hold circuit 244 or a second sample and hold circuit 245. Both sample and hold circuits 244, 245 and the switch 243 are controlled by the timing circuits 232. The output of the sample and hold circuits 244, 245 is fed to a digital multimeter 234 with calibration control 236 and displayed on a digital display 221.

In use, a first reading is taken when the immunological reaction is initiated and the switch 243 is operated by the circuit 232 such that the output from the peak detector 231 is fed to the first sample and hold circuits 244. At a pre-set time after this first reading, a second reading is taken and is fed to the second sample and hold circuits 245. The output from the first sample and hold circuits is fed to a zero reference pin on the multimeter 234 and so the output from the second sample and hold circuits 245 can be displayed to give the change in scatter intensity after said pre-set time interval, the zero reading being used to compensate for any scatter from the sample which is not due to the immunological reaction.

Figure 7:
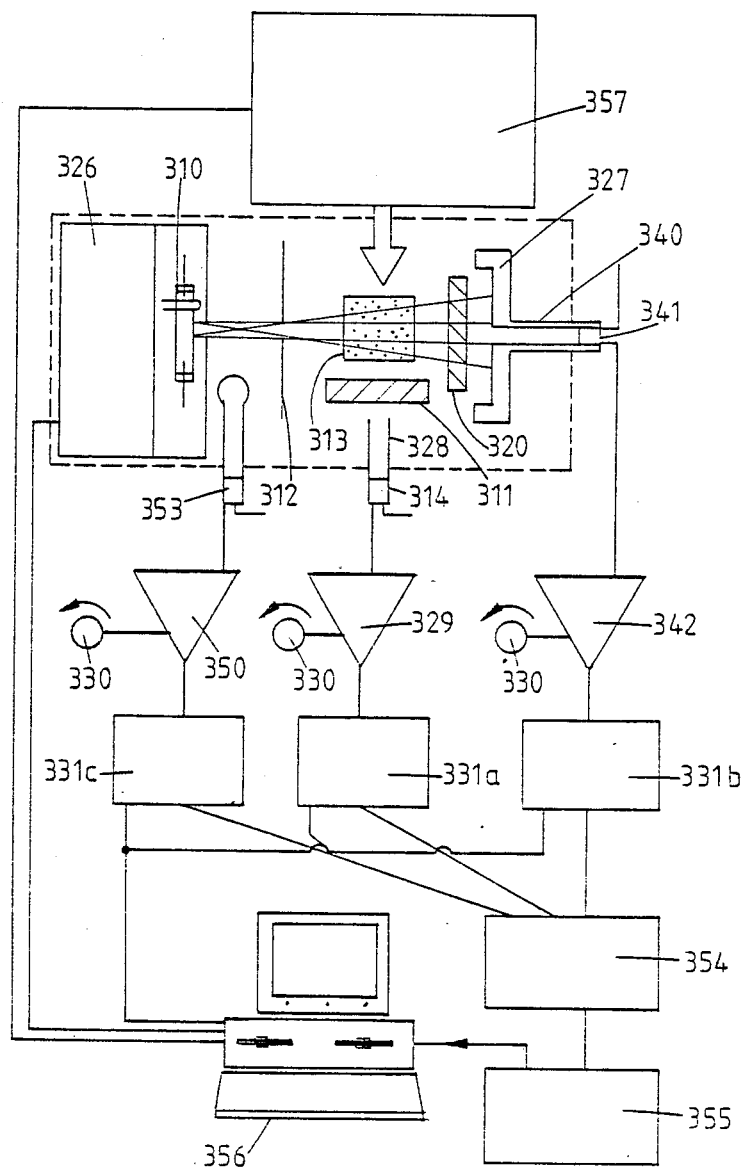
FIG. 7 is a block diagram of an apparatus according to the present invention interfaced with a micro-computer for control and result analysis purposes.

In FIG. 7 parts corresponding to these parts shown in previous drawings are given the same reference numerals in the 300 series. The apparatus shown in FIG. 7 is controlled by a micro computer which handles timing control and data analysis operations.

In addition to the detectors 314 and 341, an incident light detector 353 is included to measure the incident light from the tube 310. This can be used to improve the accuracy of the apparatus. The output from each detector 314, 341, 353 is fed to an associated amplifier 329, 342, 350 and then to a respective peak detector 331a, 331b, 331c. The output from each peak detector 331a, 33ab, 331c is fed to a multiplexer 354 and then to an analogue to digital converter 355 which is connected to a micro computer 356. The micro computer 356 replaces the timing circuits shown in previous embodiments and also controls sample processor 357 which can process the sample accurately before the readings are taken and so improve overall accuracy.

When there is high interference to the signal from the complex due to other proteins, it is preferable to use a rate determining method. In this case, measurements are taken at specific time intervals after the blood sample and the antigen are mixed. Typically, a number of readings over a few seconds and the detected signals are fed to data analysis means which allows determination of the rate of formation of the antigen/antibody complex and hence the concentration of the antibody.

Although the present invention has been described with relation to determination of antigen content, it will be clear that this method may also be employed to determine the content of a first antigen protein in a sample of blood by utilizing one or more other antibodies which is specific to the first antibody.

We claim:
1. A method of quantifying, in a whole blood sample in which red cells are lysed, an antigen or antibody which will react with a reagent to form an antigen-antibody complex, comprising the steps of:
   mixing said sample with said reagent to obtain said complex;
   exposing said sample to a source of radiation;
   measuring the intensity of radiation scattered through a given angle by said complex, the wavelength of said radiation being selected from the range 460–530 nm; and
   relating the measured intensity to the amount of antigen or antibody in said sample.

2. A method as claimed in claim 1, wherein the intensity of said scattered radiation is measured at time intervals, to determine the rate of formation of said antigen-antibody complex.

3. A method as claimed in claim 1, wherein the wavelength of radiation is selected from the range 460–510 nm.

4. A method as claimed in claim 1 in which said radiation is obtained from a xenon flash tube.

5. A method as claimed in claim 1 in which an antigenic protein is quantified.

6. A method as claimed in claim 5 in which said protein is an immunoglobulin.

7. A method of quantifying, in a whole blood sample in which red cells are lysed, a protein which will react with a reagent to form an antigen-antibody complex, comprising the steps of:
   mixing said sample with said reagent to obtain said complex;
   exposing said sample to a source of radiation;
   measuring the intensity of radiation scattered through a given angle by said complex, the wavelength of said radiation being such that the ratio of the intensity of detected scattered radiation to that of the radiation absorbed by haemoglobin from said lysed red cells is maximized; and
   relating the measured intensity to the amount of protein in said sample.

8. A method as claimed in claim 7 in which said radiation is obtained from a xenon flash tube.

9. A method as claimed in claim 7 wherein the intensity of the scattered radiation is measured at time intervals, to determine a rate of formation of said antigen-antibody complex.

10. A method as claimed in claim 7 in which said protein is an immunoglobulin.

* * * * *